US011229418B2

(12) United States Patent
Patel et al.

(10) Patent No.: US 11,229,418 B2
(45) Date of Patent: Jan. 25, 2022

(54) SYSTEM FOR GENERATING SYNTHETIC APERTURE ULTRASOUND IMAGES DURING NEEDLE PLACEMENT

(71) Applicant: The Johns Hopkins University, Baltimore, MD (US)

(72) Inventors: Nisu Patel, Franklin Park, NJ (US); Ernest Scalabrin, Northvale, NJ (US); Karun Kannan, Westford, MA (US); Kush Gupta, Baltimore, MD (US); Larissa Chan, San Francisco, CA (US); Mateo Paredes, Shoreview, MN (US); Melissa Lin, San Marino, CA (US); Shayan Roychoudhury, Madison, CT (US); Suraj Shah, S. Burnsville, MN (US); Abhay Moghekar, Baltimore, MD (US); Emad M. Boctor, Baltimore, MD (US); Nicholas J. Durr, Baltimore, MD (US); Younsu Kim, Baltimore, MD (US); Haichong K. Zhang, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 308 days.

(21) Appl. No.: 16/098,410

(22) PCT Filed: May 2, 2017

(86) PCT No.: PCT/US2017/030660
§ 371 (c)(1),
(2) Date: Nov. 1, 2018

(87) PCT Pub. No.: WO2017/192603
PCT Pub. Date: Nov. 9, 2017

(65) Prior Publication Data
US 2019/0117187 A1  Apr. 25, 2019

Related U.S. Application Data

(60) Provisional application No. 62/330,724, filed on May 2, 2016.

(51) Int. Cl.
A61B 8/12  (2006.01)
A61B 8/08  (2006.01)
(Continued)

(52) U.S. Cl.
CPC .............. *A61B 8/12* (2013.01); *A61B 8/0841* (2013.01); *A61B 8/4483* (2013.01);
(Continued)

(58) Field of Classification Search
None
See application file for complete search history.

(56) References Cited

U.S. PATENT DOCUMENTS 7,931,594 B2 *  4/2011  Hirsh ....................... A61B 8/12
                                                    600/454
2002/0156376 A1 * 10/2002  Wang ................ A61B 17/3403
                                                    600/439

(Continued)

FOREIGN PATENT DOCUMENTS

JP  2010-068923 A    4/2010
JP  2014-150928  *  1/2013
(Continued)

OTHER PUBLICATIONS

PCT International Search Report and Written Opinion of the International Search Authority corresponding to PCT/US2017/030660, dated Jul. 5, 2017, 11 pages.

Primary Examiner — Amelie R Davis
Assistant Examiner — Marjan Saboktakin
(74) Attorney, Agent, or Firm — Harrity & Harrity, LLP

(57) ABSTRACT

An aspect of the present disclosure is to provide a device or needle placement system including a needle having a proxi-
(Continued)

mal end and a distal end, and an ultrasound transducer element attached to the distal end of the needle. The system also includes a needle constraining assembly configured to receive and constrain the needle to only rotational degrees of freedom within a range of angular motion. The system further includes a needle sensor system incorporated into the constraining assembly to sense an angular orientation of the needle with the range of angular motion. The system also includes an ultrasound data processor configured to communicate with the transducer element to receive ultrasound detection signals and communicate with the needle sensor system to receive needle angular orientation signals. Based on the ultrasound detection and the needle angular orientation signals, the ultrasound data processor can calculate synthetic aperture ultrasound images.

20 Claims, 20 Drawing Sheets

(51) Int. Cl.
*A61B 8/00* (2006.01)
*A61B 34/20* (2016.01)
*A61B 10/00* (2006.01)
*A61B 17/34* (2006.01)

(52) U.S. Cl.
CPC ........ *A61B 8/5207* (2013.01); *A61B 10/0045* (2013.01); *A61B 17/3403* (2013.01); *A61B 34/20* (2016.02); *A61B 2010/0077* (2013.01); *A61B 2017/3405* (2013.01); *A61B 2017/3413* (2013.01); *A61B 2034/2059* (2016.02); *A61B 2034/2063* (2016.02)

(56) References Cited

U.S. PATENT DOCUMENTS

| 2007/0191733 | A1  |        | 8/2007 | Gianchandani et al. |            |
|--------------|-----|--------|--------|---------------------|------------|
| 2011/0106052 | A1  | *      | 5/2011 | Chiang              | A61B 8/0841 |
|              |     |        |        |                     | 604/512    |
| 2012/0123270 | A1  | *      | 5/2012 | Klee                | A61B 8/4483 |
|              |     |        |        |                     | 600/453    |
| 2016/0066883 | A1  | *      | 3/2016 | Mickelsen           | A61B 8/0841 |
|              |     |        |        |                     | 600/463    |

FOREIGN PATENT DOCUMENTS

| JP | 2014-150928 A | 8/2014 |
| JP | 2015-505696 A | 2/2015 |
| WO | WO 2013/086521 A1 | 6/2013 |

* cited by examiner

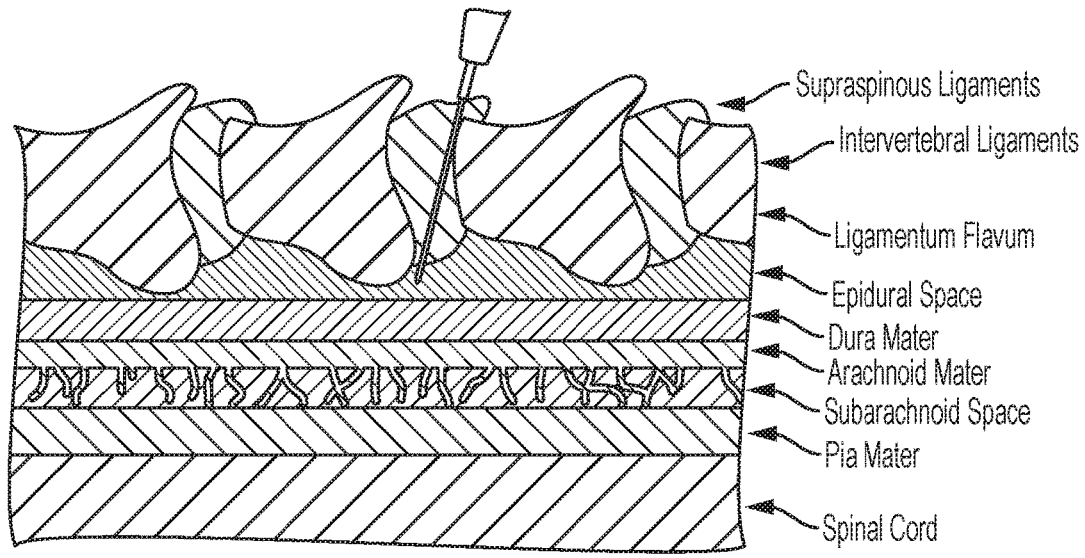
FIG. 1
(CONVENTIONAL)
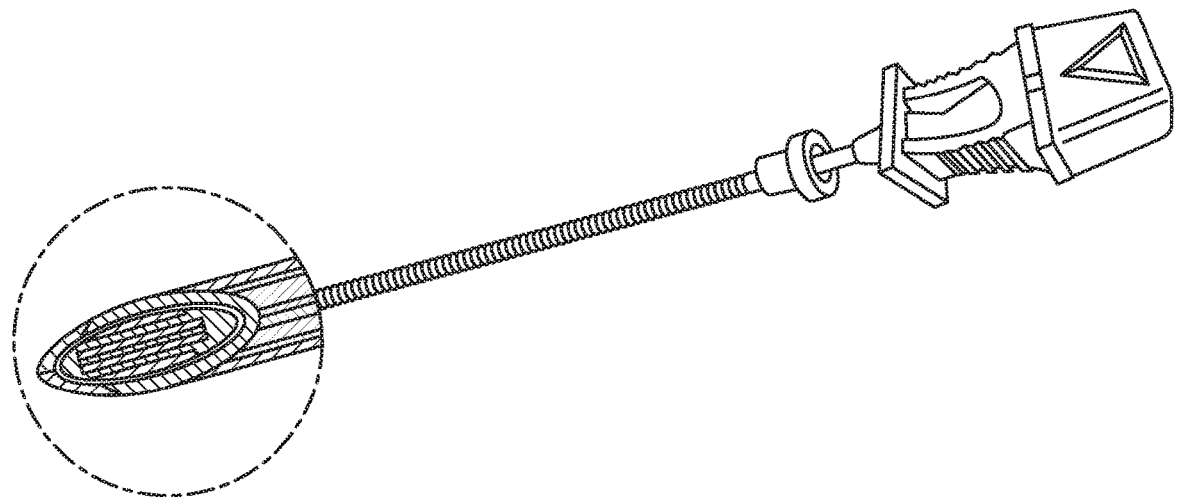
FIG. 2
(CONVENTIONAL)

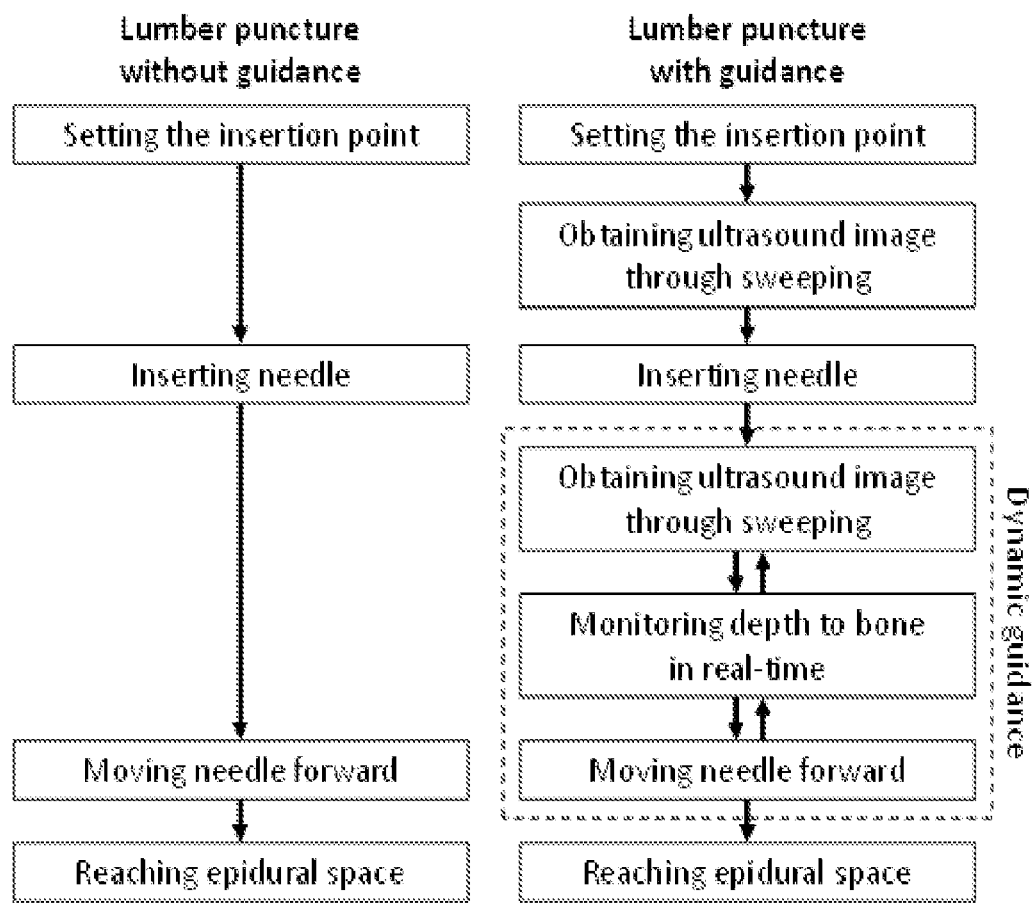
FIG. 8A (conventional)  FIG. 8B

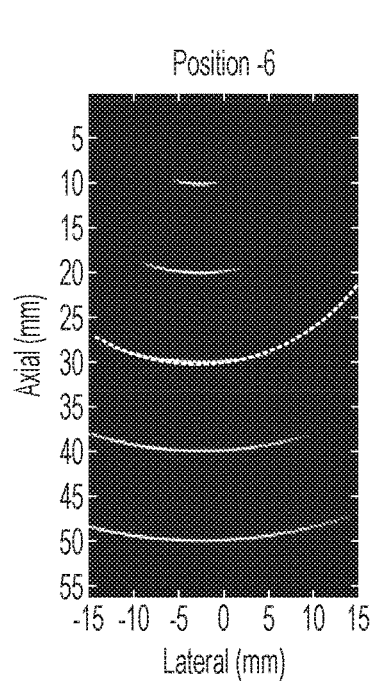 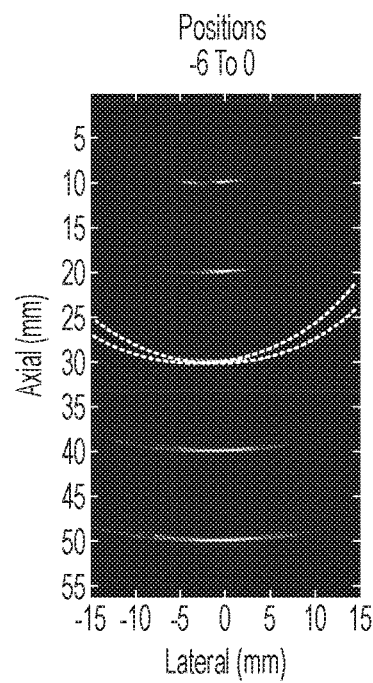 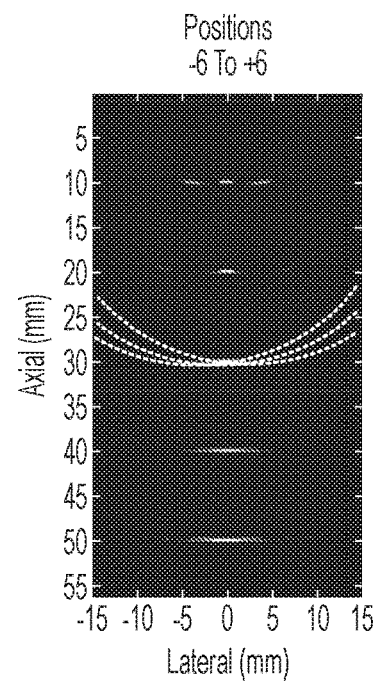
FIG. 9A          FIG. 9B          FIG. 9C
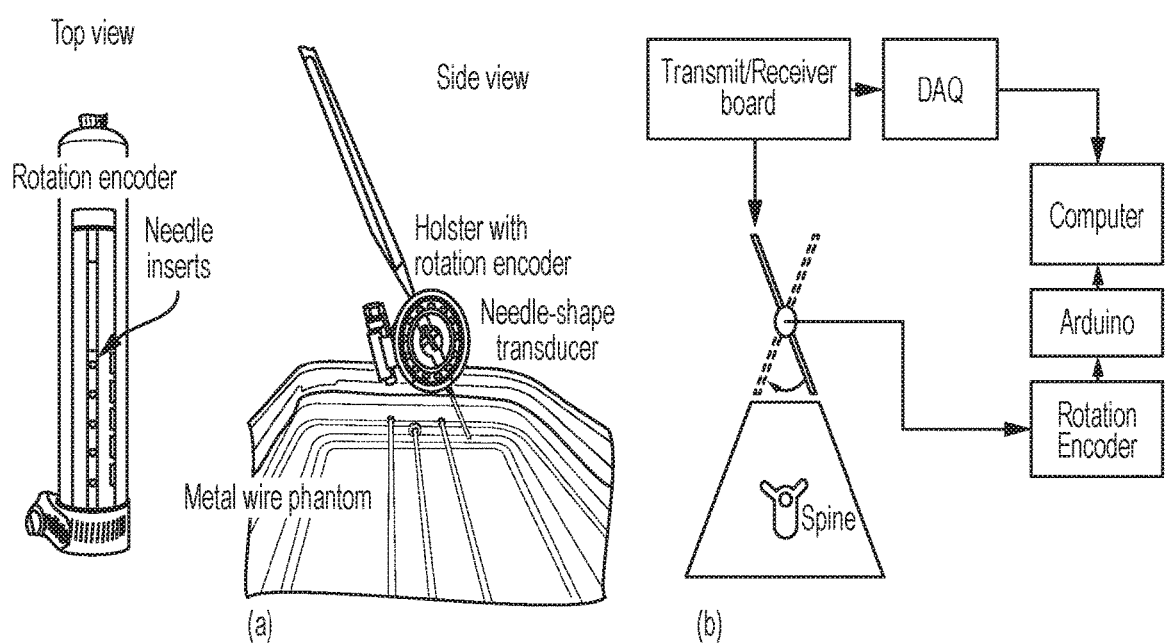
FIG. 10A          FIG. 10B          FIG. 10C

SYSTEM FOR GENERATING SYNTHETIC APERTURE ULTRASOUND IMAGES DURING NEEDLE PLACEMENT

CROSS-REFERENCE TO RELATED APPLICATIONS

This application claims priority to PCT Application No. PCT/US2017/030660, filed May 2, 2017, which claims priority from U.S. provisional patent application No. 62/330,724, filed on May 2, 2016, the entire contents of both of these applications are incorporated herein by reference. All references cited anywhere in this specification, including the Background and Detailed Description sections, are incorporated by reference as if each had been individually incorporated.

BACKGROUND

1. Field

The field of the currently claimed embodiments of the present disclosure relates to needle placement systems and in particular to a system and a method for generating synthetic aperture ultrasound images during needle placement.

2. Background

Every year, over 400,000 lumbar punctures (LPs) are performed by neurologists and emergency medicine doctors to collect cerebrospinal fluid (CSF), a vital fluid in the diagnosis of many central nervous system diseases (CNS) and conditions. To perform this procedure, a physician palpates the lower back and identifies the L3 to L5 vertebrae. Once identified, the physician proceeds to apply a local anesthetic before inserting and advancing a needle, typically 18 to 24G Quincke needle (shown in FIG. 2), through many tissue layers into the intervertebral space, as depicted in FIG. 1. FIG. 1 is a schematic representation of a longitudinal cross-section of the spinal cord of a human and an insertion of a Quincke needle through many tissue layers into the intervertebral space. FIG. 2 is a schematic representation of a conventional Quincke needle. The physician must avoid making contact with any peripheral structures, including bone, vascular tissue, and nerve bundles, on the path to the subarachnoid space, a 1 mm to 3 mm space that harbors CSF (shown in FIG. 1). The likelihood of contact with peripheral structures is increased due to the use of a beveled needle (shown in FIG. 2), which causes the needle to bend by exerting a perpendicular force during insertion. This bending phenomenon becomes a serious issue amongst obese and obstetric patients, who have a thicker layer of adipose tissue.

If the physician makes contact with these peripheral structures, the needle must be withdrawn and relocated. In addition, hitting peripheral structures in multiple attempts leads to a myriad of complications including tissue trauma, pain, post dural puncture headaches (PDPH), CSF leaks, and traumatic, or bloody, taps. Furthermore, physicians take an average of three attempts to collect CSF in a patient, and this can be even worse in obese and elderly patients. Still, the procedure is almost always performed blindly without the assistance of any imaging modalities or techniques including CT or topical ultrasound.

Therefore, there is a need for an improved system to access the subarachnoid space that reduces the number of attempts and the rate of iatrogenic complications resulting from blind entries to ensure timely diagnoses of various central nervous system (CNS) diseases.

SUMMARY OF THE DISCLOSURE

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

An aspect of the present disclosure is to provide a device or needle placement system. The system includes a needle having a proximal end and a distal end, and an ultrasound transducer element attached to the distal end of the needle. The system also includes a needle constraining assembly configured to receive and selectively constrain the needle to only rotational degrees of freedom within at least a range of angular motion. The system further includes a needle sensor system incorporated into the needle constraining assembly to sense an angular orientation of the needle with the at least range of angular motion. The system also includes an ultrasound data processor configured to communicate with the ultrasound transducer element to receive ultrasound detection signals and configured to communicate with the needle sensor system to receive needle angular orientation signals. The ultrasound data processor is further configured to calculate synthetic aperture ultrasound images based on the ultrasound detection signals and the needle angular orientation signals.

BRIEF DESCRIPTION OF THE DRAWINGS

FIG. 1 is a schematic representation of a longitudinal cross-section of the spinal cord of a human and an insertion of a Quincke needle through many tissue layers into the intervertebral space;

FIG. 2 is a schematic representation of a Quincke needle;

FIG. 8A depicts a flow diagram of a procedure of inserting a needle without guidance, as is performed conventionally;

FIG. 8B depicts a flow diagram of a procedure of inserting a needle with guidance, according to an embodiment of the present disclosure;

FIGS. 9A, 9B and 9C show corresponding poses or images in a back projection process, according to an embodiment of the present disclosure;

FIG. 10A depicts a top view of rotation encoder with a plurality of needle inserts, according to an embodiment of the present disclosure;

FIG. 10B is a side view of the rotational encoder a metal wire phantom simulating a location of an object such as a spine, according to an embodiment of the present disclosure;

FIG. 10C is logic flow diagram of a hardware integration for a single element STRATUS system, according to an embodiment of the present disclosure;

DETAILED DESCRIPTION

Some embodiments of the current disclosure are discussed in detail below. In describing embodiments, specific terminology is employed for the sake of clarity. However, the disclosure is not intended to be limited to the specific terminology so selected. A person skilled in the relevant art will recognize that other equivalent components can be employed and other methods developed without departing from the broad concepts of the current disclosure. All references cited anywhere in this specification, including the Background and Detailed Description sections, are incorporated by reference as if each had been individually incorporated.

To aid clinicians performing deep needle placements (lumbar punctures, spinal anesthesia, epidurals, etc.), a system or device is provided to enable dynamic guidance in the form of ultrasound images to reduce iatrogenic complications and the chance of placement failure. In an embodiment, the device generates a high-resolution image from a single piezo-crystal and an external system to measure the angle of the needle with respect to the patient. As the needle is inserted, a clinician would rock the needle back and forth to effectively sweep an image of the trajectory of the needle. This image would contain information about the type, size, and distance of obstacles in the path of the needle, as well as the location of the intended target anatomical structure.

Figure 3:
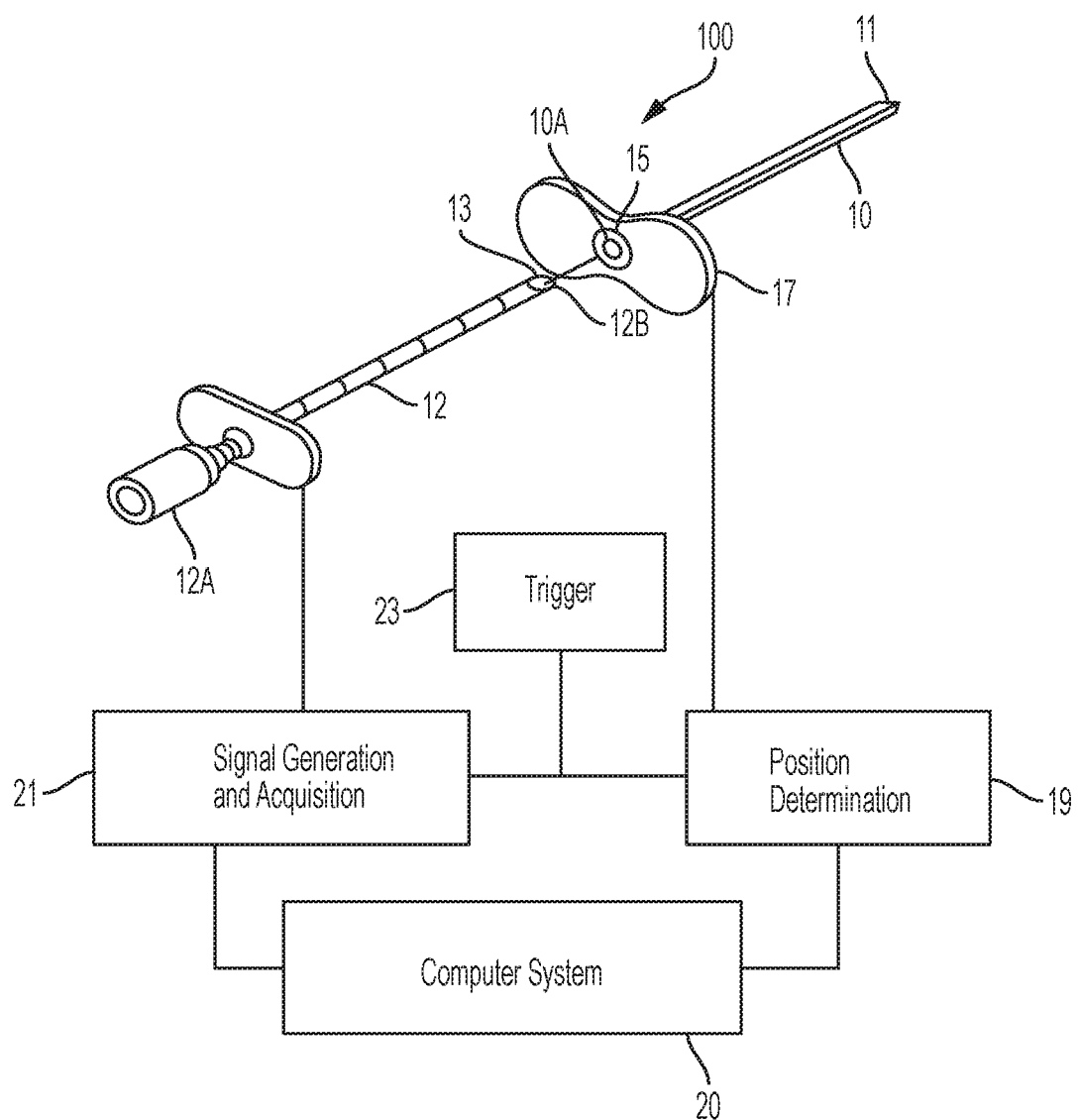
FIG. 3 depicts a device including a needle guide for guiding the insertion of a needle into a patient, according to an embodiment of the present disclosure.

FIG. 3 depicts a device 100 including needle guide 10 for guiding the insertion of a needle 12 into a patient (shown in FIG. 4), according to an embodiment of the present disclosure. Typically, ultrasound probes require arrays of crystals to generate images. The individual sensors are fired all at once for a traditional ultrasound image, or with a delay for phased-array images. Synthetic aperture imaging simulates this by moving the array sensor to various locations. At each location, the array fires a pulse and receives back an echo. While synthetic aperture imaging is an old technique, the methods have always employed linearly or radially displacing an array of transducer elements using a mechanically actuated mechanism. This array would fire at fixed increments, and the resulting signal can be synthesized to form an image.

In an embodiment of the present disclosure, the ultrasound imaging device 100 instead relies on a single sensor element (transceiver) 13 that is passively displaced in an arc defined by a user. In an embodiment, the sensor element (transceiver) 13 is placed at a tip 12B of the needle 12. Because the user generates movement, an external measurement system is provided that relies on a position encoder 15. The position encoder 15 is provided within a holster 17 at an end 10A of needle guide 10. The holster 15 also holds the needle guide 10. In addition, the holster 17 houses position determination system 19 of the position encoder 15. In an embodiment, the position encoder 15 is an optical encoder which includes an optical sensor. However, as it must be appreciated other types of position encoders can also be used, including for example, magnetic, electronic or mechanical encoders. With traditional synthetic aperture imaging, the location of the array is always known because the system autonomously controls movement. The present ultrasound imaging device 100 replicates this through repeated physical measurements of the position and transformations of the measured quantities. In an embodiment, the needle 12 is configured to lock its translation to prevent translation of the needle 12 within the needle guide 10 along the axis of the needle guide 10 and this further insertion into a body of a patient. However, the needle 12 is configured to rotate within the needle guide 10. In an embodiment, the needle guide 10 is a hollow tube that is configured to receive the needle 12. In an embodiment, an internal diameter of the needle guide is slightly larger than an external diameter of the needle 12 to facilitate insertion of the needle 12 into the needle guide 10. In an embodiment, a longitudinal length of the needle guide 10 is shorter than a longitudinal length of the needle 12 to enable a tip 12B of needle 12 to extend farther than a tip 11 of the needle guide 10.

Normally, synthetic aperture imaging has the benefit of multiple receive elements, thereby generating a low-resolution image. In fact, most synthetic aperture systems rely on either a single transmit element or a subarray of transmitters to send a pulse and use the entire array as receive elements to generate multiple signals per firing. These can be added up over different transmit elements to produce a high-resolution image. However, because there is a limited space within the needle 12, as space is available for only a single transceiver element 13 that switches in between transmit and receive modes, correction is thus implemented to account for this movement and synthesize an image given only noisy A-scans.

Device 100 overcomes the depth and movement issues by placing ultrasound sensors at or near the tip or end 12B of the needle 12. Currently, ultrasound sensors (transceivers) only enter the body in intravascular ultrasound (IVUS) catheters. In these catheters, a linear array of sensors is spun in a circular motion around the circumference of the catheter to provide a radial view into vein walls. The device 100, according an embodiment of the present disclosure, uses a single sensor/transceiver 13 imaging straight along the longitudinal axis of the needle 12. Instead of an actuator to move or rotate the sensor/transceiver 13, we rely on the physician or user to rock the needle 12. This will sweep the sensor/transceiver 13 in an arc around the longitudinal axis of the needle 12.

The device 100 also includes a position determination system 19 in communication with the position encoder 15. The position encoder 15 and associated position determination system 19 is constructed and arranged to measure the angle of the needle 12 and thus the angle of the transceiver 13 with respect to the holster 17 which is immobile or fixed relative to the patient for each time the transceiver (e.g. transducer) 13 is fired. Because the geometry of the needle 12 is known, the position of the transceiver 13 within the needle 12 can be calculated from the angle measured outside of the body of the patient using the position determination system 19.

The ultrasound transceiver 13 includes an ultrasound transducer or transmitter and an ultrasound receiver or sensor. The ultrasound transceiver 13 is connected to signal generation and acquisition system 21. In an embodiment, the signal generation and acquisition system 21 is connected to transceiver 13 via a connection point provided at or near an end 12A of the needle 12. In an embodiment, the signal generation and acquisition system 21 is configured to send a pulsed signal to the transceiver 13 (transducer) to drive the transceiver 13 (transducer) to generate ultrasound pulses. Furthermore, in an embodiment, the signal generation and acquisition system 21 is further configured to receive ultrasound waves received or detected by the transceiver 13 (sensor). In an embodiment, for example, the signal generation and acquisition system 21 includes a pulsing circuit to send a train pulses with a frequency of, for example, 5 MHz to drive the ultrasound sensor/transceiver 13.

The device 100 further includes a triggering circuit 23 to activate the position measurement system 19 and the signal generation and acquisition 21 substantially simultaneously (e.g., within few microseconds or less). The device 100 also includes computer system 20 having therein image synthesis software to generate a coherent image from the ultrasound sensor/transceiver 13 output and the angle measurement. The computer system 20 is in communication with the signal generation and acquisition system 21 and position determination system (e.g., angle determination system) 20. The computer system 20 receives input signals from both the position determination system 19 (which provides the position or angle of the needle relative to the fixed holster 17 or fixed needle guide 10) and from the signal generation and acquisition system 21 (which provides signals corresponding to ultrasounds detected by the transceiver 13). The computer system 20 builds an ultrasound image based on these input signals.

Figure 4:
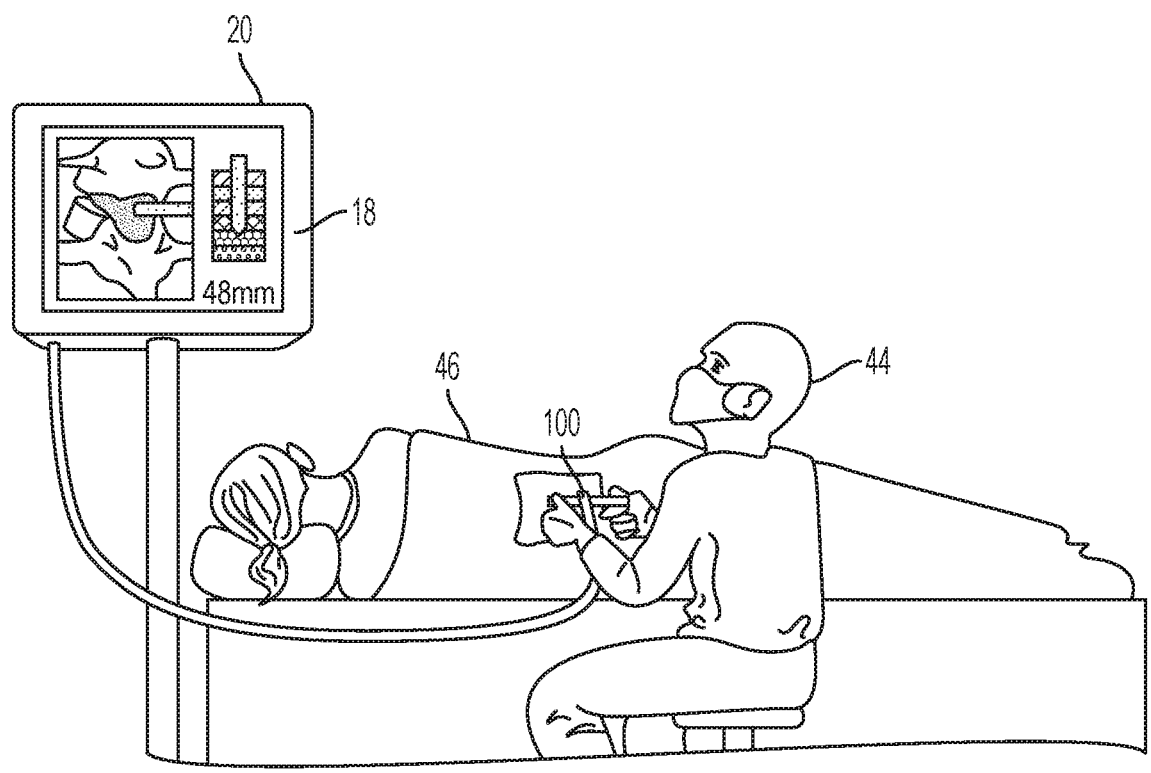
FIG. 4 depicts an example use of the needle guide and needle of the device in a clinical setting, according to an embodiment of the present disclosure.

FIG. 4 depicts an example of the device 100 in a clinical setting wherein health practitioner (e.g., physician, clinician, surgeon, etc.) 44 is inserting the needle 12 of device 100 using the needle guide 10 into a spinal cord of a patient 46 while visualizing an image showing a location of the needle 12 or needle guide 10 on screen 18 of computer system 20, according to an embodiment of the present disclosure. Specifically, in operation, a clinician 44 would prepare a patient 46 using normal clinical procedures. After the area of placement of needle 12 is cleaned and aestheticized, the clinician 44 would initially penetrate a centimeter under the skin using the needle guide 10. The clinician 44 would then thread the needle 12 through the holster 17 and through end 10A (lumen) of needle guide 10 until the needle 12 extends beyond the tip 11 of needle guide 10. The clinician 44 would rotate the needle 12 inside the needle guide 10. The transceiver within the tip 12B of needle 12 would emit ultrasound waves and receive ultrasound echoes that would be measured and converted into an electrical signal using signal generation and acquisition system 21.

The clinician 44 would rock the needle 12 back and forth and generate an initial image of the surrounding tissue. From this image, the physician 44 would be able to determine whether the placement is on midline, and whether the needle 12 is on track to penetrate the intervertebral space. Furthermore, any obstacles in the path of the needle 12 would also be visible. The clinician 44 can then continue inserting the needle 12. An image can be obtained on screen 18 of computer system 20 at any point by simply wiggling the needle 12. The clinician or physician 44 would continue the intended operation until reaching a desired area of the body of the patient 46. For example, the physician or clinician 44 may perform this operation to collect cerebrospinal fluid.

Therefore, as it must be appreciated, the present ultrasound imaging device 100 includes software to convolve the images using algorithms based on the position given by the external position (e.g., angle) determination system 19. This is a novel feature because in the present case traditional delay-and-sum methods may not provide desired results. Normally, because the array is actuated, there is a constant velocity to generate a fixed distance between successive firings. Instead, in the present configuration, we can have variable velocities and periods of quick acceleration and deceleration are expected. These algorithms must accept A-scans as opposed to low-resolution images that a traditional synthetic aperture algorithm would accept.

Ultrasound provides a real-time, nonionizing imaging modality to help guide physicians. While topical ultrasound is widely used in many aspects of clinical procedures, it has a few severe limitations when used for deep needle placements. Firstly, image quality degrades very rapidly with imaging depth. Imaging deeper structures with ultrasound may pose a significant issue due to the low signal to noise ratio and degraded resolution. This hinders the utility of topical ultrasound to guide physicians during lumbar punctures, which may require fine resolution up to 14 cm deep. Furthermore, patient movement also hinders the use of pre-procedural ultrasound. Because the skin surface moves at a different rate than the spinal structures, a clinician cannot use these images to place and guide the needle. Therefore, the present device 100 can solve these and other problems by providing a reference position which in this case may be the needle guide 10 or the holster 17 as both the needle guide 10 and the holster 17 are fixed and do not move during the rotation or angular movement of the needle 12.

In an embodiment, the transceiver 13 may comprise for example a piezo-electric element to construct an A-line signal in the path of the needle 12 to identify a distance and type of tissue ahead, essentially acting as a "stud-finder." By allowing the health practitioner 44 to distinguish tissue ahead of the needle 12, the health practitioner 44 can avoid hitting any obstacle. In fact, this actually turns needle bending, which is a significant hindrance to accurate placement of a needle in a conventional setting, into an advantage in the present disclosure. Clinicians (health practitioner 14) would be able to steer the needle 12 passively due to needle bending to avoid hitting peripheral structures in a trajectory of the needle 12. Currently, there is no guidance system that is unhindered by needle depth and bending. Additionally, some embodiments of the current disclosure can be integrated into the current workflow of emergency rooms (ERs) and operating rooms (ORs), because it can accommodate any needle 12 a physician 44 prefers. This could greatly improve the efficacy of lumbar taps while driving down the frequency of complications, resulting in savings for both hospitals and patients by avoiding unnecessary procedures and diagnostic delays.

Figure 5:
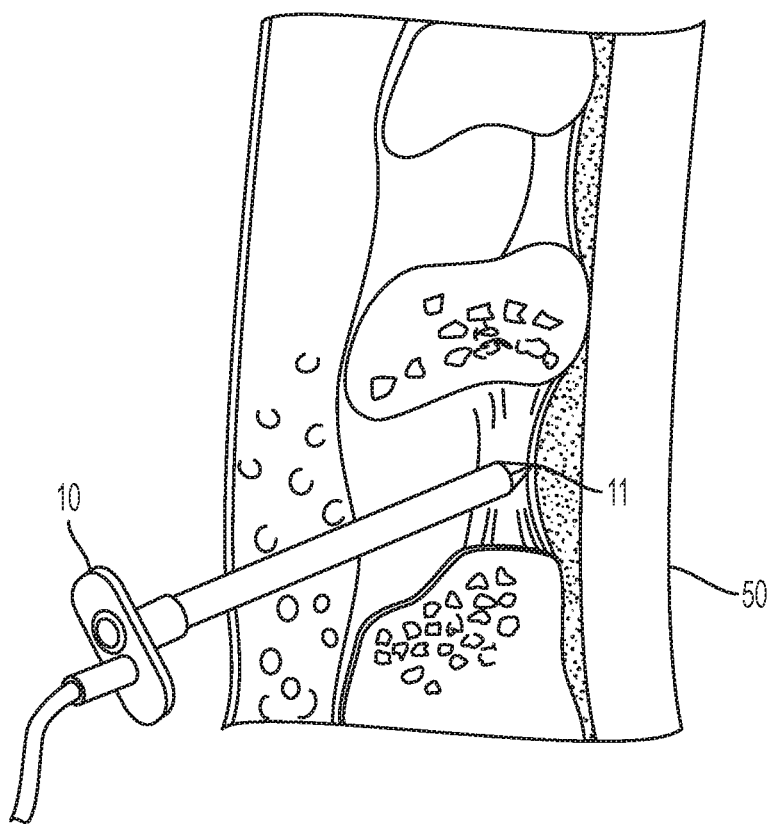
FIG. 5 depicts a detailed longitudinal cross-sectional view of a spinal cord showing a location guidance using the needle guide, according to an embodiment of the present disclosure.

FIG. 5 depicts a detailed longitudinal cross-sectional view of a spinal cord 50 showing a location guidance using the needle guide 10 having the ultrasound imaging device, according to an embodiment of the present disclosure. For example, the needle guide 10 can be inserted by the clinician 44 to certain depth where the clinician 44 is comfortable would not reach any undesired area with the body of the patient. After insertion of the needle guide 10 up to a certain depth, the clinician 44 can then insert the needle 12 inside the hollow needle guide 10 and push the needle 12 such that the tip 12B of needle 12 reaches or slightly extends beyond tip 11 of needle guide 10. After performing this initial step, the clinician 44 can then further use the device 100 and the method described herein to push and guide the tip 12B if the needle 12 further inside the body of the patient 46.

Figure 6:
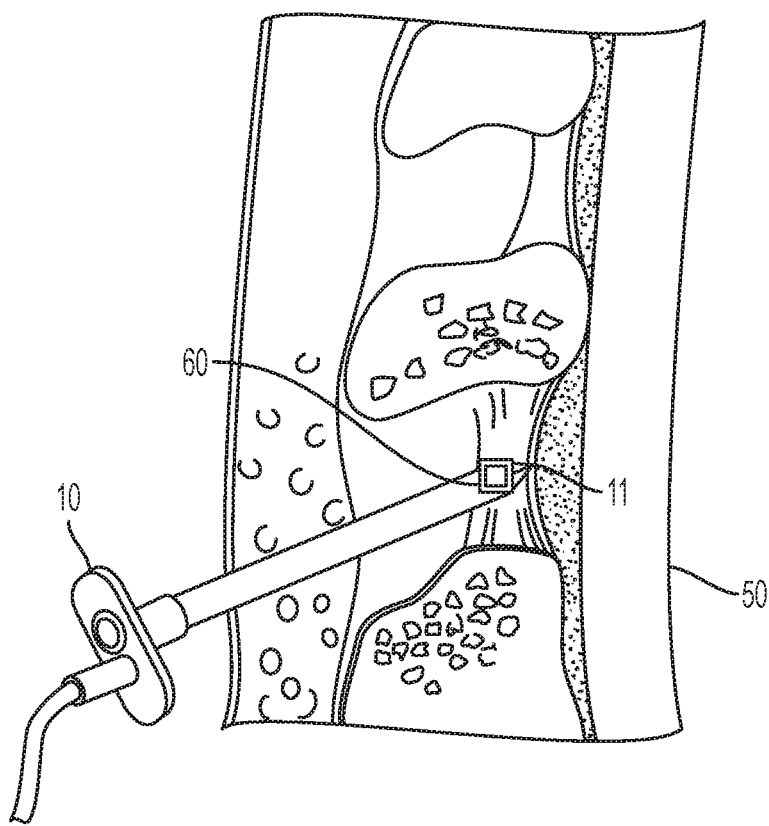
FIG. 6 depicts a detailed longitudinal cross-sectional view of a spinal cord showing a location guidance using a needle guide having an ultrasound imaging device, according to another embodiment of the present disclosure.

FIG. 6 depicts a detailed longitudinal cross-sectional view of a spinal cord 50 showing a location guidance using the needle guide 10 having the ultrasound imaging device, according to another embodiment of the present disclosure. In this case, contrary to the example shown in FIG. 5 and described in the above paragraph, the needle guide 10 includes a transceiver 60. The transceiver 60 may be similar to the transceiver 13 describe in the above paragraphs. The transceiver 60 is also configured to emit ultrasound pulses and detect ultrasound echoes. An initial ultrasound image can be constructed using the position of the tip 11 of the needle guide and the ultrasound waves emitted and detected by the transceiver 60. In this case, instead of inserting the needle guide 10 without any guidance, the clinician 44 is able to initially assess or determine or see an approximate or initial position of the tip 11 of the needle guide 10. This provides increased precision in placement and guidance when inserting the needle 12. Furthermore, this may provide a means to reaching increased depths in the body, for example, during cancer treatment in tissue located deep in the body of the patient, etc.

While the current device is described herein for use in lumbar punctures, the image guidance can be used for any deep needle placements. For example, epidural placement is a very similar procedure used to inject anesthesia into the epidural space, a space that is a few millimeters above the subarachnoid space. Other similar procedures include spinal anesthesia, neuraxial blocks, peripheral blocks, cerebral ventricular shunts, and central line placements.

The following paragraphs describe example embodiments of the current disclosure in more detail. However, the broad concepts of the current disclosure are not limited to only these examples. Further embodiments can include, but are not limited to the following approaches to determining the position of the needle tip:

1. COMPUTER VISION: Any system by which a camera and image analysis software are used to track and calculate, either directly or indirectly, the location of the external shaft of the needle, from which the position of the needle tip is interpolated. For example, using a camera positioned upon the device to detect an external landmark (an April tag or any other asymmetric sticker) to derive needle position, or using an external unmounted camera to detect the needle itself through video-tracking software.
2. RADIO TRIANGULATION: Any system that involves the emission of radiowaves from multiple points along the body of the needle, and the use of external sensors to triangulate the source of the radio waves to ascertain the position of the needle tip within the body.
3. OPTICAL MEASUREMENT: Any System that utilizes optical measurements to determine the position of the ultrasound element at the tip of the needle. This can include using laser guidance or light to measure distance by bouncing light, including lasers, off of mirrors or other surfaces, or beaming light to detectors to determine the position of the needle. Another embodiment may include shining light into a fiber optic cable and detecting the light bouncing back, indicating the angle of the cable.
4. ULTRASOUND TRIANGULATION: Any use of ultrasound to detect the position of an element with respect to ultrasound sources or detectors with known position, both inside and external to the body
5. HALL EFFECT: Any system that involves the magnetization of the device and subsequent detection of disruptions within the local magnetic field to triangulate the position of the piezoelectric element within some micro-neighborhood.
6. ACCELEROMETER and GYROSCOPE: Any system that utilizes an accelerometer and gyroscope to measure the motion of the device, and from this derive the ultimate position of the device in space.

Clinical adoption of the present device and its entry into secondary markets can be envisioned due its practicality and ease of use. These markets include, for example, epidurals, spinal anesthesia, neuraxial blocks, peripheral nerve blocks, and central venous line placements, etc. We have gathered input from neurologists, anesthesiologists, radiologists, and emergency medical personnel at every design stage.

Needle Fabrication: One challenge we face is manufacturing the ultrasound-embedded needle to be inserted into the patient. This may involve the microfabrication of a PZT crystal onto a 14G Quincke needle. Additionally, the crystal may need to be connected to a pulsing circuit in the signal generation and acquisition system 21 through two wires, an input and an output. The input will send a pulse train of, (for example 5 MHz) while the output contains the signal representing the measured echoes. Although the pulse train implemented in this example is 5 MHz, as it can be appreciated, other pulse trains with different frequencies are also within the scope of the present disclosure. For example, a pulse train with a frequency greater or smaller than 5 MHz is also within the scope of the present disclosure.

A piezo-electric (PZT) crystal in a 1 mm diameter needle can be fabricated. In a 14G needle which has a diameter of 2.108 mm, the space is double than 1 mm, thus allowing us to also fabricate a PZT crystal in a 14G needle. However, it can be noted that the geometry of an epidural needle is different from a lumbar puncture needle. Therefore, the piezo-electric crystal may be configured according to the conformation of the dimension of the needle 12.

External Angle Measurement System: Another component of the system is an external device to measure the angle of the needle with respect to the patient. The system is preferably unobtrusive to a user while restricting the degrees of freedom to 2 (side-to-side rotation in the horizontal axis, and insertion into the patient in the z-direction). Additionally, synthetic aperture imaging may use the distance between successive pulses to be less than the wavelength divided by two. Using our intended frequency of 5 MHz as an example and the speed of sound in the body, given by equations (1), the wavelength is calculated using equation (2).

$$f = 5*10^6 \text{ Hz}; c = 1540 \frac{m}{s} \qquad (1)$$

$$\frac{\lambda}{2} = \frac{c}{2f} = 150 \text{ microns} \qquad (2)$$

To achieve a position resolution of 154 microns at a depth of 4 cm, the value of angular resolution is calculated by equation (3) as follows.

$$\theta_{res} = \tan^{-1} \frac{154 \text{ micron}}{4 \text{ cm}} = 0.22 \text{ degrees} \qquad (3)$$

To achieve this resolution, a rotary encoder with 4096 pulses per revolution can be employed, achieving roughly twice the needed resolution. Optical encoders are well suited for this application. In an embodiment, the holster 17 can be designed to contain the assembly including the position determination system 19 to measure the angle with respect to a surface. In an embodiment, an optical encoder is used to measure the position as it offers a relatively high frame rate for measurements.

Synthesis Software: The needle 12 can send and receive echoes, while simultaneously the angle of the needle 12 is measured. The software implementation in the computer system can be configured to take the signals from both the position determination system 19 and the signal generation and acquisition system 21 and generate or synthesize an image based on the measured angle/position and the detected echoes.

However, as described above, in an embodiment, the device uses a single piezo-electric crystal as opposed to an array of piezo-electric crystals to receive the signal. This is different from any other synthetic aperture imaging device which often uses a single transmit element and multiple receive elements. Furthermore, the software can also be configured to use various signal filtering and coherence algorithms that allow a noisy signal to be built into a relatively high-resolution image based on the commonalities of the signal from neighboring positions.

To test the complete system, three phantoms are built to sequentially test the imaging. All of these phantoms use a ballistics gel substrate because this gelatin is biofidelic to adipose tissue. The first of these phantoms consists of a single, thick metal wire cast in ballistics gel. The system or device is used to insert a needle at half centimeter increments in the ballistics gel and rock the needle through a 15 degree sweep. The metal wire can be modeled as a point source of echoes and the resulting image will be an approximated point spread function (PSF) of the system. A PSF is useful as it allows analysis into important quantities of interest, like contrast, lateral resolution, and axial resolution. Furthermore, the simple phantom allows easy troubleshooting.

After retrieving the PSF from the first phantom, the system is used on a second phantom consisting of a well-defined two-dimensional structure of metal wires in the ballistics gel. Because the configuration is known (a square or a circle, for example), the same shape can be retrieved on the obtained ultrasound image. The two-dimensional structure of wire is a natural progression from the first phantom.

Finally, the last bench test involves an adolescent spine cast in ballistics gel. The spine consists of the five lumbar vertebrae, each articulating to a different degree, on Nylon wire. The intervertebral discs are modeled through silicon 60, a polymer that is biofidelic to cartilage. This structure is a complex 3 dimensional structure and allows one to generate images that include the features needed to guide physicians. These sets of images can be presented to clinicians to determine which features are most important for successful entry into the intervertebral space. Because each vertebrae is articulated to a different amount, characterizing the intervertebral heights needed for successful guidance can be obtained.

Figure 7:
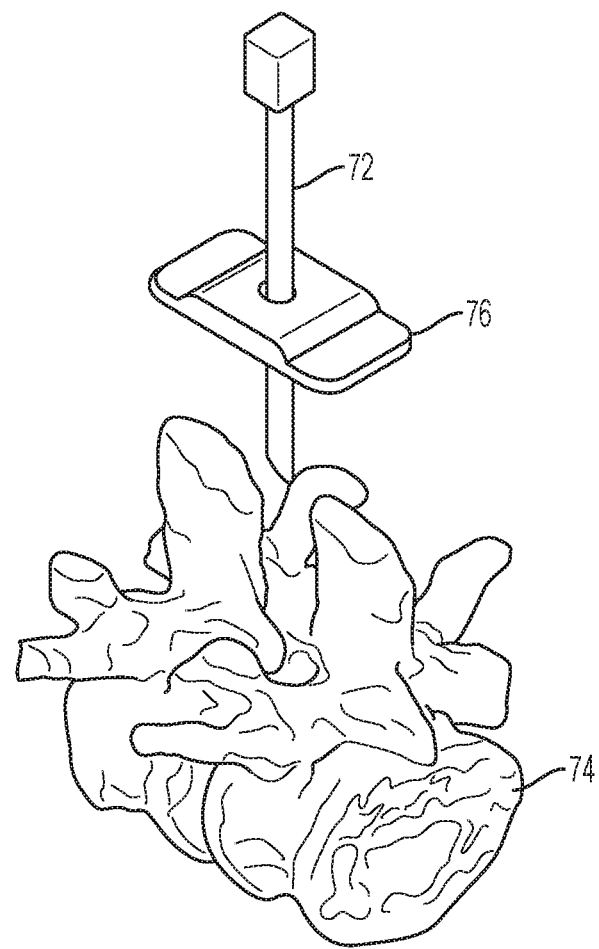
FIG. 7 depicts a concept of a single element Synthetic TRacked AperTure UltraSound (STRATUS) system, according to an embodiment of the present disclosure.

FIG. 7 depicts a concept of a single element Synthetic TRacked AperTure UltraSound (STRATUS) system, according to an embodiment of the present disclosure. FIG. 7 shows a needle 72 with respect to a spine 74. An attachment 76 is provided to guide the needle 72 through the spine 74. The attachment may include sensors and various mechanisms and will be described further in detail in the following paragraphs. The system includes two subsystems: a needle-shape ultrasound probe, and a tracking system. As described in the above paragraphs, the tracking system includes the holster and encoders. The system includes an insert that can fit inside a Quincke needle. The insert has a piezoelectric (PZT) element embedded at the tip of the needle 72, with a magnet wire backing material (not shown). In an embodiment, the needle 72 is fabricated using a stainless steel tube with a magnet wire threaded there through, with one end of the magnet wire connected to the PZT element and the other end soldered to a coaxial cable with a BNC connector. A tracking system is used to track the position of the needle. In an embodiment, as described in the above paragraphs, an angular encoder is used to track the 1-degree-of-freedon (DOF) rotational motion. The needle 72 itself provides an A-line real-time feedback to a user, so that the contrast from bone could be used for the warning to prevent the needle from collision. An ultrasound image of a slice of the scanning trajectory can be formed during the procedure, which can aid in determining the direction the needle 72 should proceed.

FIG. 8A depicts a flow diagram of a procedure of inserting a needle without guidance, as is performed conventionally. FIG. 8B depicts a flow diagram of a procedure of inserting a needle with guidance, according to an embodiment of the present disclosure. For a practical procedure, as shown in FIG. 8A, the conventional blind insertion can be categorized into finding insertion, actual insertion, forward motion of the needle penetrating the subarachnoid space, and cerebral spinal fluid (CSF) collection. On the other hand, according to an embodiment of the present disclosure, as shown in in FIG. 8B, the image/sensing guidance can take place at any intermediate step. First, the physician palpates the patient's back, as in the current standard of care. Once the initial entry point has been determined, the tracking holster 76 is placed on the back of the patient at the determined location. When the holster 76 is secured, the physician threads the needle 72 through the holster 76 into the patient. To generate an image, the physician sweeps the needle 72 in an arc, a motion similar to one that is already needed in navigating the needle for a blind procedure. The adipose and connective tissues surrounding the spine are soft and they simply move out of the way of the needle while sweeping, so tissue damage is not a concern. This sweeping motion allows the present system to collect data from both the needle probe and the tracking holster 76. As the algorithm processes this data, the image is updated on the screen for the physician to use in real-time. The physician is then able to sweep again at a deeper layer to produce another image. During the insertion of needle 72, the distance from bone (e.g., bone in spine 74) to the needle 72 can be updated in real-time and the surrounding structures can be imaged by sweeping the needle 72 at any time. In addition, the position of the needle 72 within the image can be updated in real time from the encoder. After reaching the dura, the ultrasound element insert can be pulled out and a regular lumbar puncture atraumatic needle (22, 24 or 26G) threaded in to puncture the dura for CSF collection, creating a small hole in the dura and minimizing the possibility of iatrogenic complications arising. In this way, it is possible to safely perform a lumbar puncture while avoiding structures along the way to the subarachnoid space.

In an embodiment, a proposed imaging approach is based on the accurate tracking of the element location informed by a 12-bit absolute magnetic angular encoder (AEAT-6012). The angular encoder is able to provide absolute angle detection with a resolution of 0.0879°. The angular encoder has no upper speed limit, though there will be fewer samples per revolution as the speed increases. In an embodiment, the encoder is connected to an 'encoder-to-tube' adapter, which allows the pivot angle of the needle 72 to directly correspond to the angle of read by the encoder. The current design incorporates an Arduino UNO which collects the encoder angle while an oscilloscope collects from the element itself.

Utilizing rotation/pivot angle information, a synthetic aperture focusing is applied to reconstruct a 2D ultrasound image. All rotation angle positions are accumulated and form a virtual ultrasound array with curvilinear scanning. The collected radio-frequency (RF) data are mapped into polar coordinates, and a back projection process is applied based on the virtual array. The relationship between pre and post reconstruction can be formulated as equations (4) and (5).

$$y_{bf}(m, n) = \sum_e y_{bf_e}(m, n, e), \qquad (4)$$

$$y_{bf}(m, n, e) = y_{pre}(d, e), \qquad (5)$$

where $y_{bf}$ is the final reconstructed RF data, $y_{bf_e}$ is the reconstructed RF data from single position, and $y_{pre}$ is the received raw RF data. m, n are the pixel information of the lateral and axial direction, respectively. The distance in the pre-beam formed data is d, and the received element number is e. The received signal distance is related to the actual image geometry from equation (6).

$$d^2 = m^2 + n^2. \qquad (6)$$

For each element position, this back projection is repeated. FIGS. 9A, 9B and 9C show corresponding poses or images in a back projection process, according to an embodiment of the present disclosure. FIG. 9A shows a position −6 degree from the center pose back-projected. FIG. 9B shows positions in the range from −6 degree to 0 degree position back-projected and summed. FIG. 9C shows positions in the range from −6 degree to +6 degree position back-projected and summed. The yellow line represents the back projection geometrical loci of a point at 30 mm depth point target. Therefore, the image shown in FIG. 9A shows a single element back projection is shown. As the number of poses increases, the focusing point is gradually made and the point targets get smaller. In the image shown in FIG. 9C, in which symmetric information is used, each point target is reconstructed appropriately. Envelope detection and scan conversion are applied on the beam formed image, and the final STRATUS image is displayed in Cartesian coordinates.

As described in the above paragraphs, the needle-shape ultrasound transducer is based on the PZT-5H element placed on the tip of the wire inserted in a 14G Quincke needle. The fabricated single element transducer is mounted on a holster with a rotation encoder to read precise rotational position. In an embodiment, the distance from the needle tip to the rotation pivot point is about 36 mm. The transmission is triggered by a function generator, and received ultrasound and the trigger signals are captured by an oscilloscope or data acquisition system (for example, US-Key, Lecoeur Electronique).

FIG. 10A depicts a top view of rotation encoder with a plurality of needle inserts, according to an embodiment of the present disclosure. FIG. 10B is a side view of the rotational encoder a metal wire phantom simulating a location of an object such as a spine, according to an embodiment of the present disclosure. FIG. 10C is logic flow diagram of a hardware integration for a single element STRATUS system, according to an embodiment of the present disclosure. For an experimental validation, a known trajectory is scanned. The top of the needle was attached to a Cartesian stage which is used to precisely rotate the needle and set its position. The stage allows the needle 72 to hold steady at each incremental angle step. In an embodiment, the RF data is collected nine times at each position. An averaged RF line is used at each position for synthetic image formation. In an embodiment, for freehand scanning, the needle 72 is moved freely along the rotation, and data for 500 positions for ultrasound and rotation tracking are collected. In an embodiment, the encoder and ultrasound reception is synchronized using MATLAB software (from MathWorks). The ultrasound data is collected in real-time using a data acquisition (DAQ) device. The tracking data and the ultrasound data are transferred to a PC for data processing.

Figure 11:
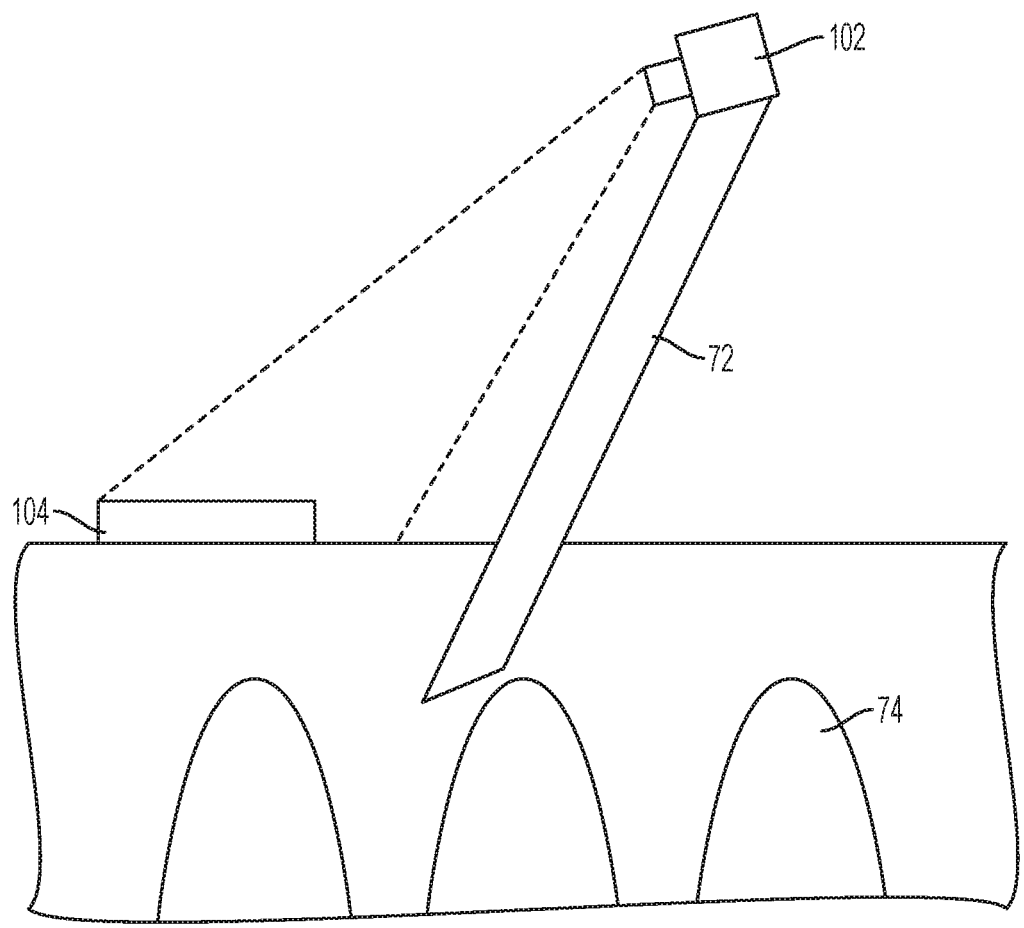
FIG. 11 depicts a device including a needle guide for guiding the insertion of a needle into a patient, according to an embodiment of the present disclosure.

FIG. 11 depicts a device including a needle guide for guiding the insertion of a needle into a patient, according to an embodiment of the present disclosure. In an embodiment, the needle guide includes a small camera 102 and a tag (e.g., April tag) 104. The camera 102 is attached or mounted to the needle 72 and is arranged to face the tag 104. The tag 104 is placed on the patient. When the needle 72 is inserted, for example in spine 74 of the patient, the needle 72 is guided so as avoid the bones of the spine 74, the motion and orientation of the needle 72 changes the orientation of the camera 102 relative to the fixed tag 104. As a result, the image information captured by the camera 102 changes with the orientation of the needle 72. An imaging processing technique can use this imaging information to provide the position of the tip of the needle 72.

Figure 12:
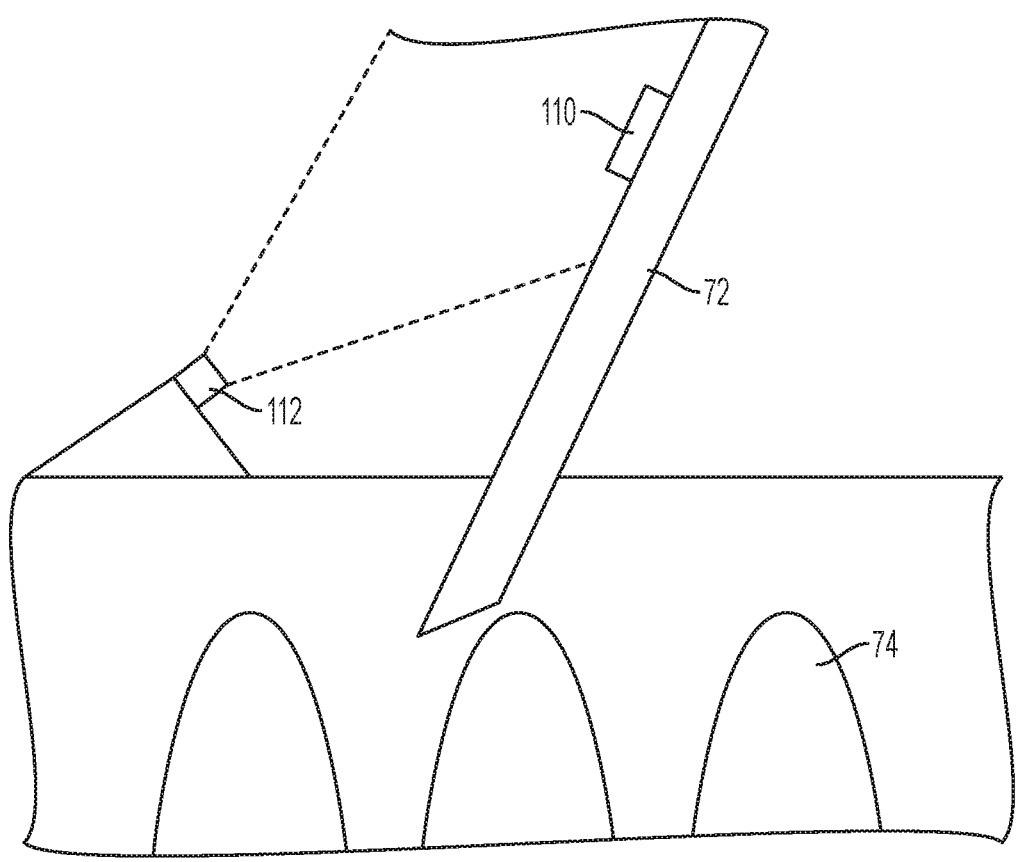
FIG. 12 depicts a device including a needle guide for guiding insertion of a needle into a patient, according to another embodiment of the present disclosure.

FIG. 12 depicts a device including a needle guide for guiding insertion of a needle into a patient, according to another embodiment of the present disclosure. In this embodiment, the tag or marker 110 is placed on the needle 72 and the camera 112 is placed on the patient. In this case, when the needle moves, the tag 110 changes its position and/or orientation relative to the camera. Similar to the above embodiment, an image processing technique can be used to extract the position of the tip of the needle 72 based on the image information captured by the camera 112.

Figure 13:
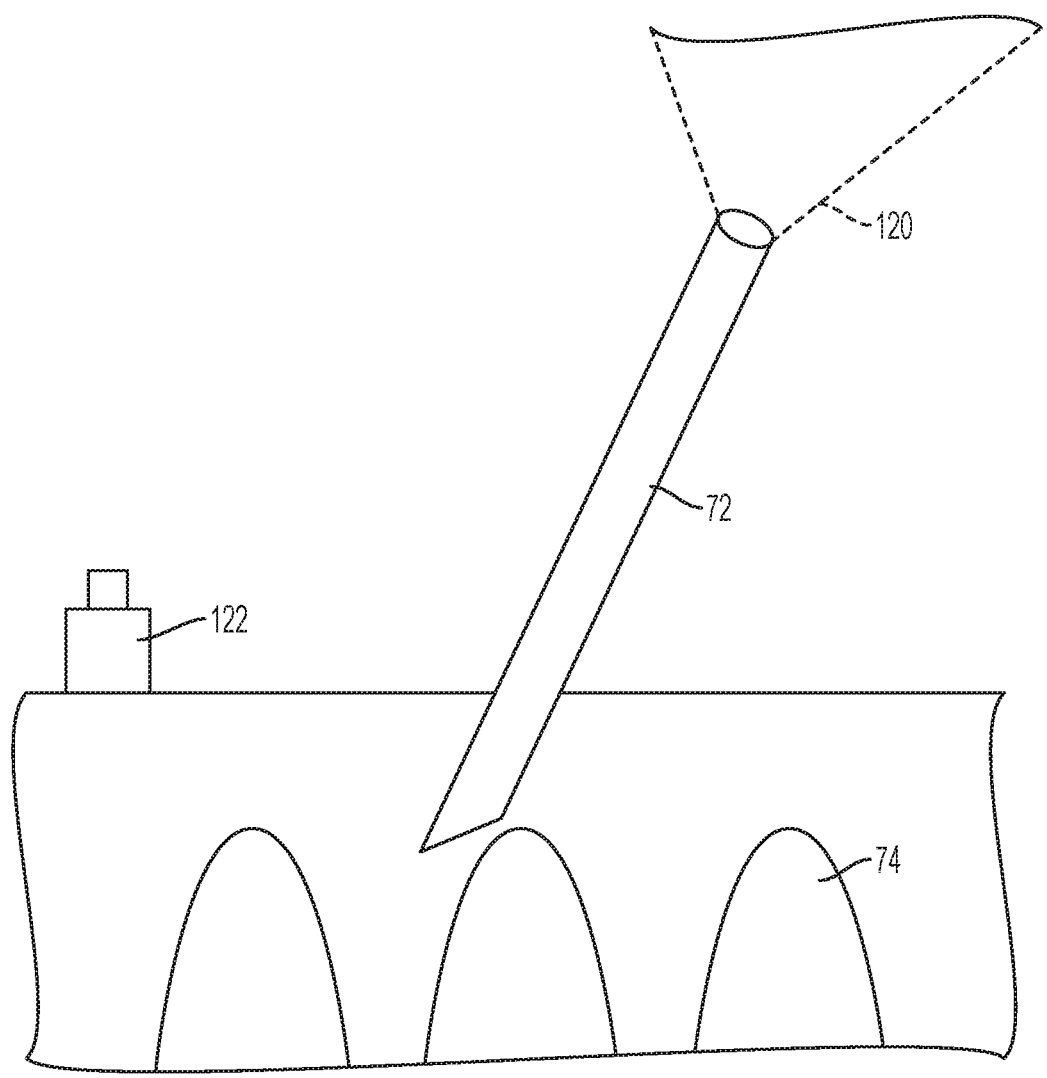
FIG. 13 depicts a device including a needle guide for guiding insertion of a needle into a patient, according to another embodiment of the present disclosure.

FIG. 13 depicts a device including a needle guide for guiding insertion of a needle into a patient, according to another embodiment of the present disclosure. In this embodiment, a projector 120 mounted on the needle 72 projects a pattern or shape on a screen, wall, or ceiling. A camera 122 is positioned on the patient tracks the pattern. As the pattern changes, the camera captures a different image information. An image processing technique can be used to extract the position of the tip of the needle 72 based on the image information captured by the camera 122.

Figure 14:
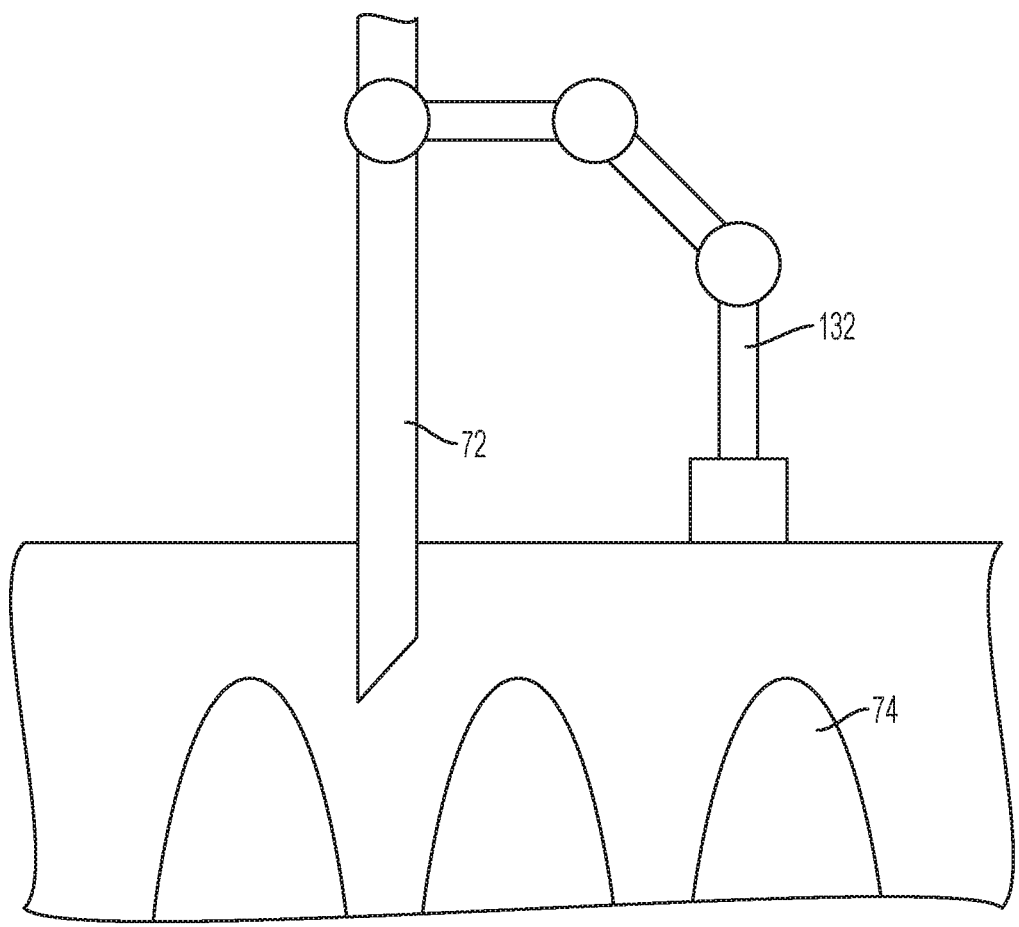
FIG. 14 depicts a device including a needle guide for guiding insertion of a needle into a patient, according to another embodiment of the present disclosure.

FIG. 14 depicts a device including a needle guide for guiding insertion of a needle into a patient, according to another embodiment of the present disclosure. In this embodiment, a mechanical arm or robot 132 can be used to guide the insertion of the needle 72 as desired in various degree of freedom (DOF). The mechanical arm or robot 132 can track the needle motion in needed degrees of freedom. In addition, the robot can also be configured and arranged to restrict motion to limit degrees of freedom.

Figure 15:
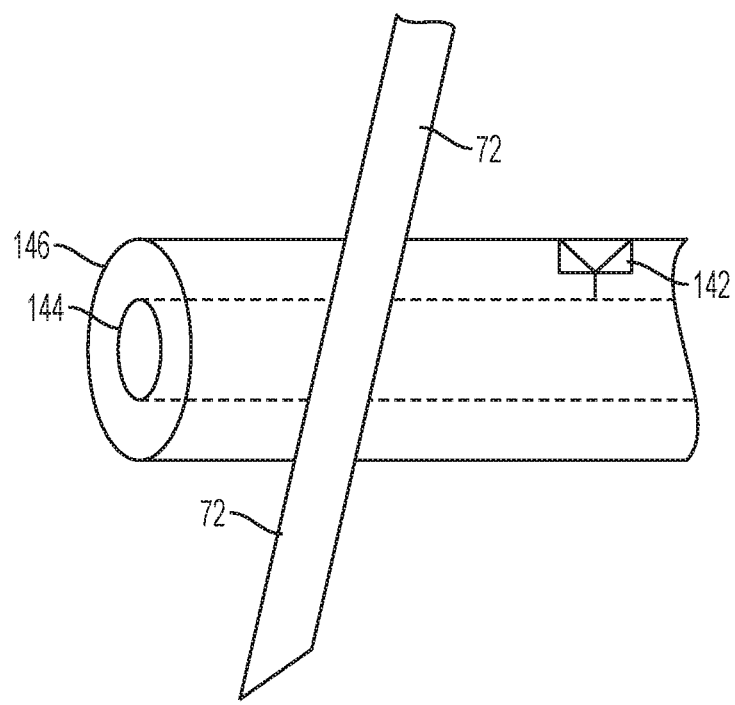
FIG. 15 depicts a device including a needle guide for guiding insertion of a needle into a patient, according to another embodiment of the present disclosure.

FIG. 15 depicts a device including a needle guide for guiding insertion of a needle into a patient, according to another embodiment of the present disclosure. In this embodiment, an optical encoder or tracker 142 is mounted to an outer cylinder 146. An inner cylinder 144 is disposed inside the outer cylinder 146. The inner cylinder rotates with the needle 72 while the outer cylinder 146 remains fixed. When the needle 72 is rotated, the inner cylinder 144 rotates with the needle 72. The optical tracker 142 reads the distance rotated by the inner cylinder 144 and thus tracks the angular rotation or orientation of the needle 72.

Figure 16:
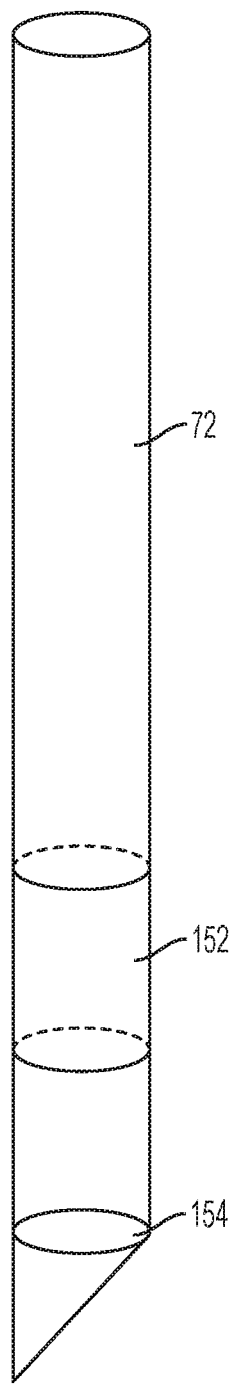
FIG. 16 depicts a configuration of a needle having an ultrasound element disposed therein, according to an embodiment of the present disclosure.

FIG. 16 depicts a configuration of a needle having an ultrasound element disposed therein, according to an embodiment of the present disclosure. In this embodiment, a side shooting or side firing ultrasound element 152 is positioned and arranged on the side of the needle 72. In addition, a front facing ultrasound element 154 is placed at the tip of the needle 72. The side firing ultrasound element 152 together with the front facing ultrasound element 154 can be used to provide a position or orientation of the needle as well as imaging of tissue or objects in front of the needle 72. For example, the side firing ultrasound element 152 can be used to provide the position or orientation through echo location while the front facing ultrasound element 154 can be used to send and receive echoes to image the tissue in front of the needle 72.

Figure 17:
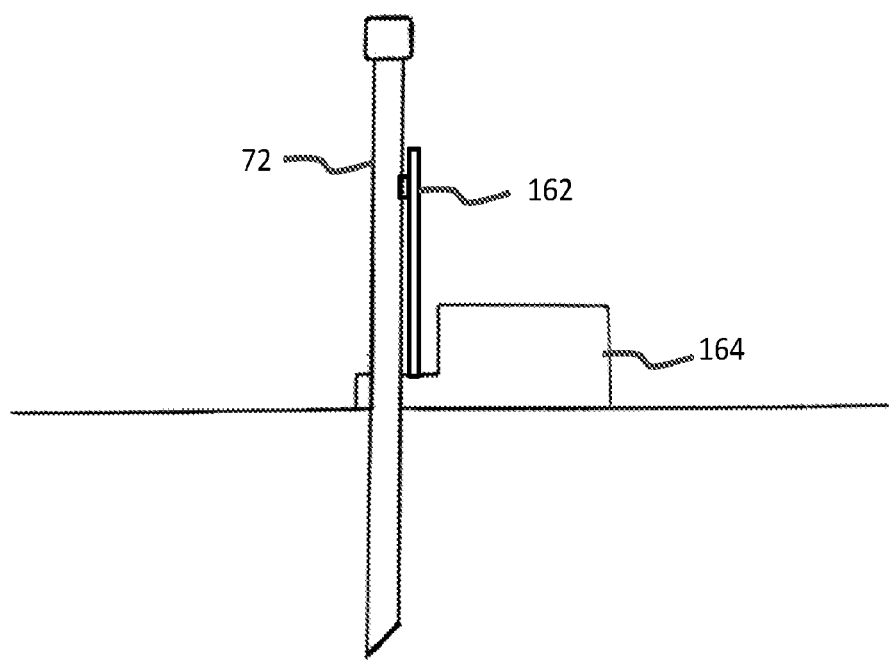
FIG. 17 depicts a device including a needle guide for guiding insertion of a needle into a patient, according to another embodiment of the present disclosure.

FIG. 17 depicts a device including a needle guide for guiding insertion of a needle into a patient, according to another embodiment of the present disclosure. In this embodiment, a linear potentiometer 162 is positioned substantially parallel to the needle 72 so as to track a depth of insertion of the needle 72 in the tissue of the patient. The potentiometer 162 is also attached on the external part of the holster 164. A slider of the potentiometer 162 is attached directly to the needle 72. A linear changing resistance of the potentiometer 162 is correlated with a change in depth of penetration of the needle 72 into the tissue of the patient.

Figure 18:
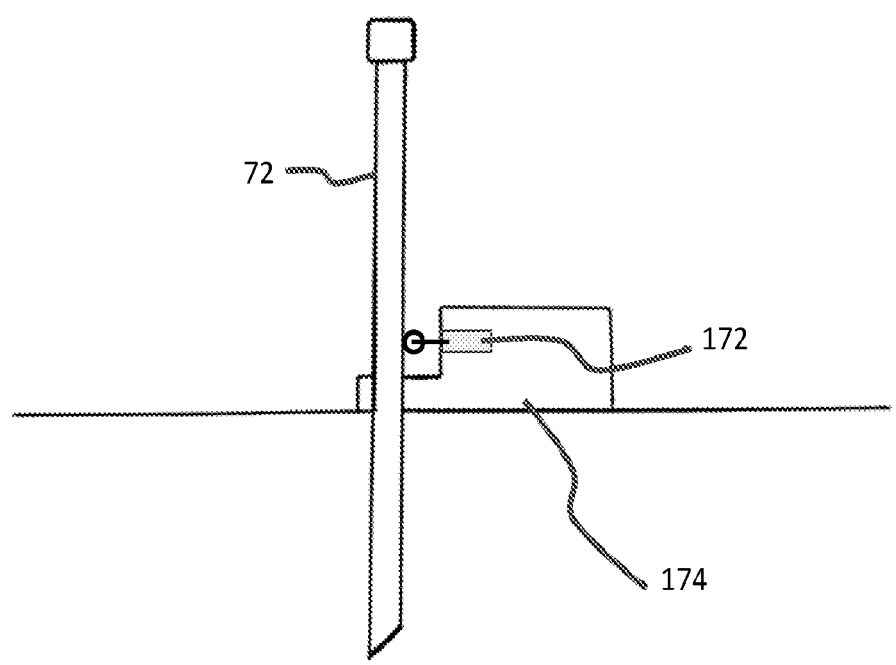
FIG. 18 depicts a device including a needle guide for guiding insertion of a needle into a patient, according to another embodiment of the present disclosure.

FIG. 18 depicts a device including a needle guide for guiding insertion of a needle into a patient, according to another embodiment of the present disclosure. In this embodiment, instead of the potentiometer 162 in the previous embodiment, a rotation encoder 172 is provided. The rotation encoder has a friction element wheel having a friction surface (e.g. rubber) that rests against the needle 72. The rotation encoder is provided as part of the holster 174. The insertion of the needle 72 rotates the wheel of the rotation encoder 172 which allows tracking of the insertion depth of the needle 72. In other words, a movement in depth of the needle 72 is translated into a rotation of the wheel or friction element of the rotation encoder 172. A number of revolution performed by the wheel can be converted by the encoder into a linear distance or depth.

Figure 19:
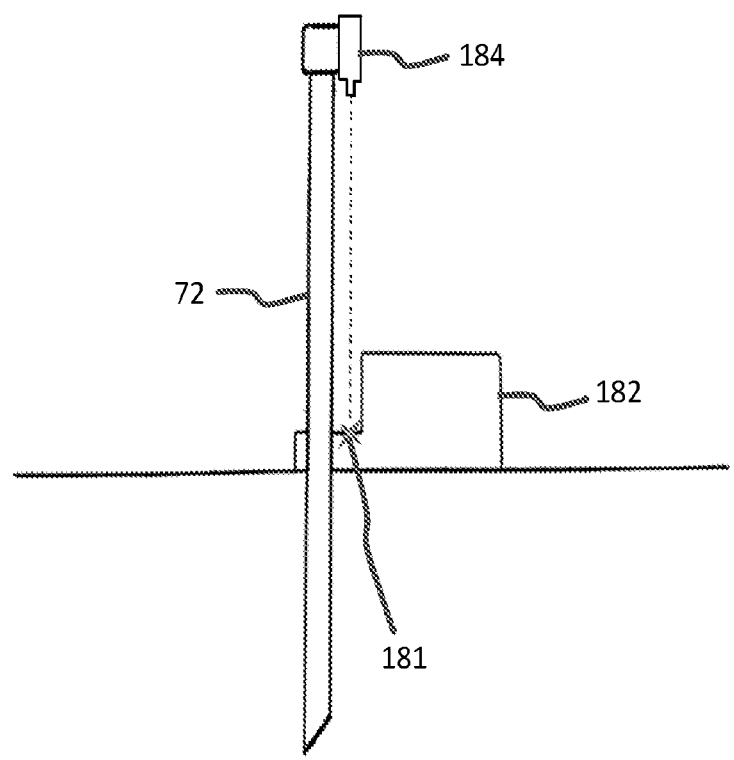
FIG. 19 depicts a device including a needle guide for guiding insertion of a needle into a patient, according to another embodiment of the present disclosure.

FIG. 19 depicts a device including a needle guide for guiding insertion of a needle into a patient, according to another embodiment of the present disclosure. In this embodiment, an optical sensor (e.g., IR sensor) 184 is placed on the needle 72. In an embodiment, the optical sensor 184 is attached to the head of the needle 72 and oriented to point downwards. Light (e.g., IR light) emitted from a light emitting device 182 provided in holster 182 is transmitted towards the optical sensor 184 and the light is detected by the optical sensor. By measuring the time it took to detect the light, a distance from the light emitting device to the optical sensor can be found. As a result, a depth of penetration of the needle 72 into the tissue of the patient can be measured.

Figure 20:
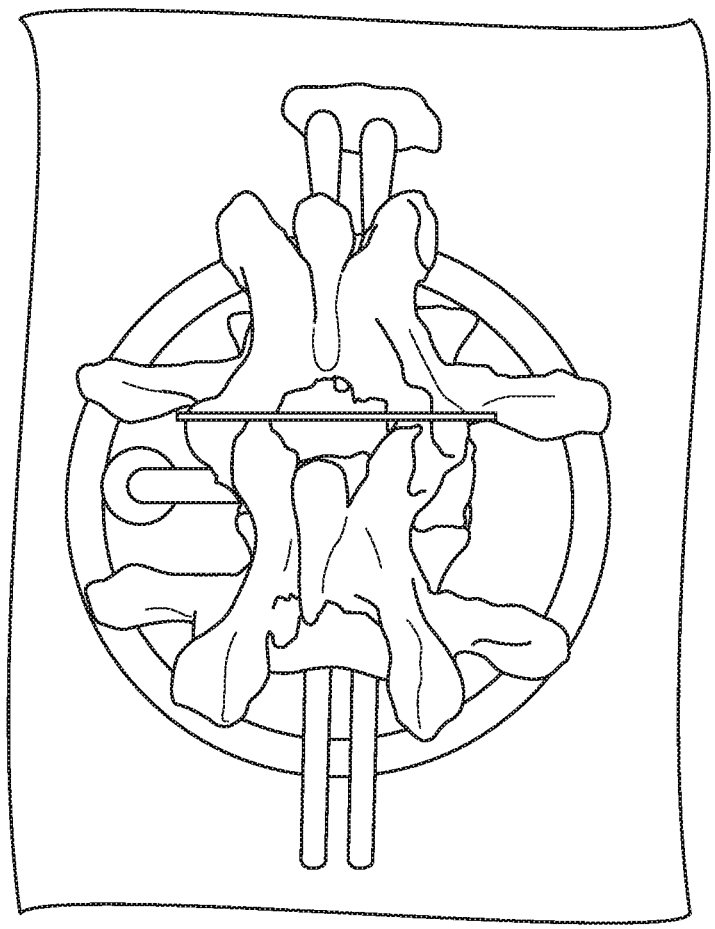
FIG. 20 shows a setup of a spinal phantom experiment with adolescent human vertebra, according to an embodiment of the present disclosure.

FIG. 20 shows a setup of a spinal phantom experiment with adolescent human vertebra, according to an embodiment of the present disclosure. The horizontal bold line represents the plane that is imaged. This plane includes a window between two spinous processes and the interlocking facets on the sides.

Figure 21:
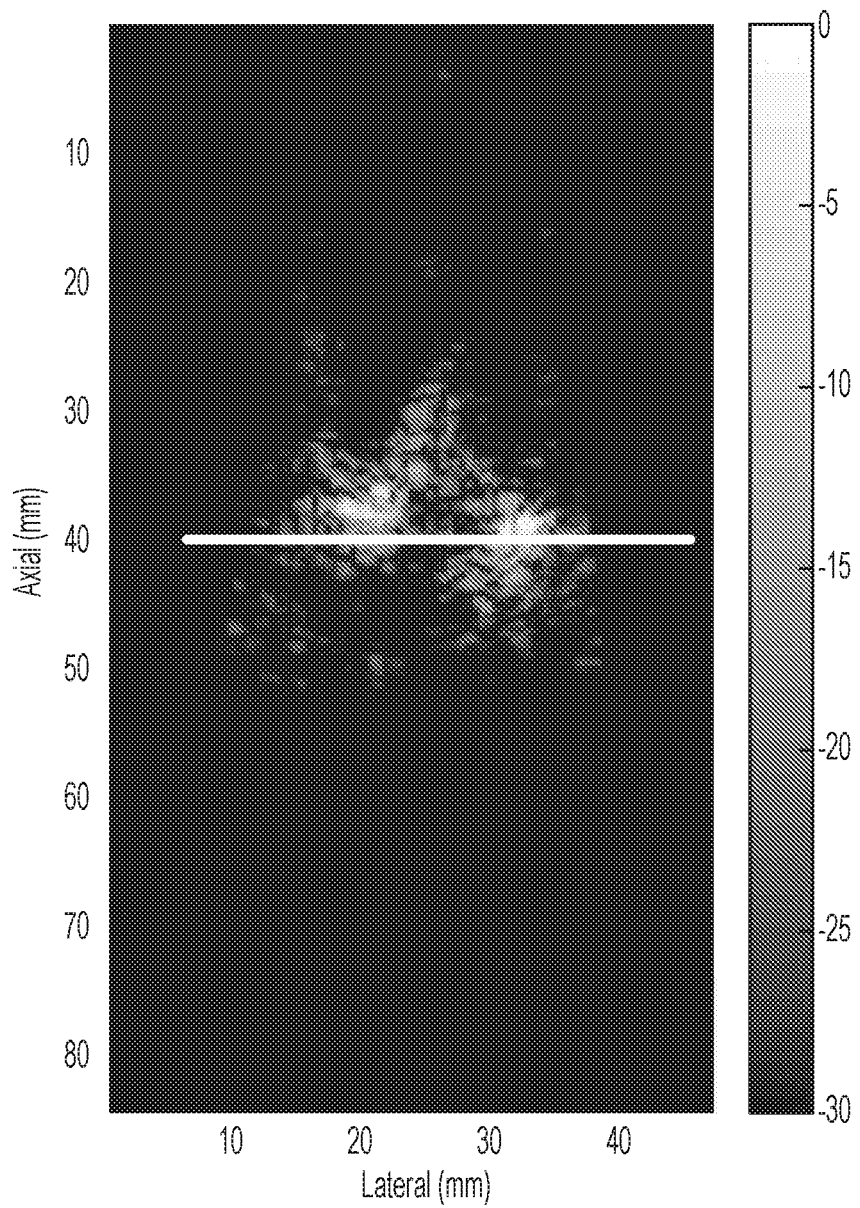
FIG. 21 shows a B-mode image at the horizontal line plane obtained with the present device or system described herein, according to an embodiment of the present disclosure.

FIG. 21 shows a B-mode image at the horizontal line plane obtained with the present device or system described herein, according to an embodiment of the present disclosure. The image shows a gap in the middle between the interlocking facets, which are the two bright spots on the left and right.

Figure 22A:
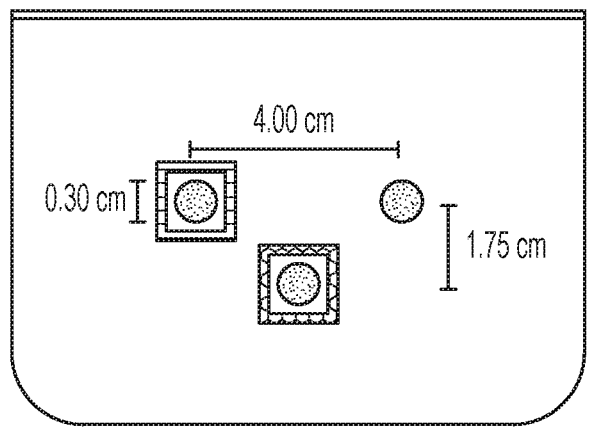
FIG. 22A is cross section view of the wire phantom experimental setup for testing the device having the needle, according to an embodiment of the present disclosure.

FIG. 22A is cross section view of the wire phantom experimental setup for testing the device having the needle, according to an embodiment of the present disclosure. Each black circle represents a wire. A distance between the wires and a diameter of the wires is indicated in FIG. 22A. The wires that are surrounded by boxes correspond to the two wires that are within the field of view of our device.

Figure 22B:
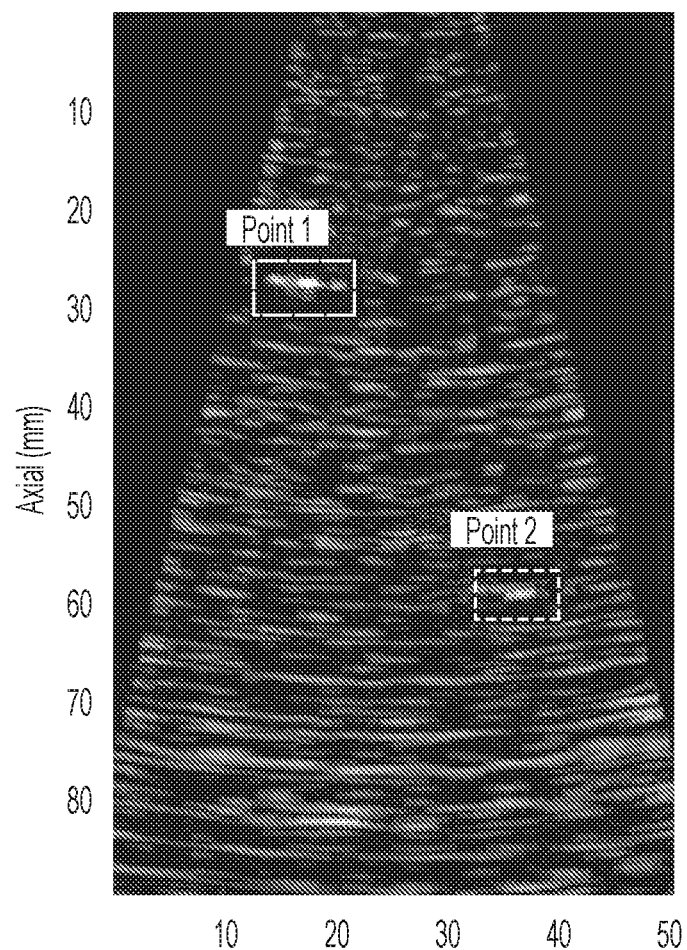
FIG. 22B shows a resulting ultrasound image of the wire phantom experiment obtained using the device including the needle, according to an embodiment of the present disclosure.

FIG. 22B shows a resulting ultrasound image of the wire phantom experiment obtained using the device including the needle, according to an embodiment of the present disclosure. The boxed points (Point 1 and Point 2) correspond to the two imaged wires shown in FIG. 22A. FIG. 22B shows that the two wires simulating the bones are detected and well accounted for using the device and system described herein.

As it must be appreciated from the above paragraphs, there is provided a device or needle placement system. The system includes a needle having a proximal end and a distal end; and an ultrasound transducer element attached to the distal end of the needle. The system also includes a needle constraining assembly configured to receive and selectively constrain the needle to only rotational degrees of freedom within at least a range of angular motion. The system further includes a needle sensor system incorporated into the needle constraining assembly to sense an angular orientation of the needle with the at least range of angular motion. The system also includes an ultrasound data processor configured to communicate with the ultrasound transducer element to receive ultrasound detection signals and configured to communicate with the needle sensor system to receive needle angular orientation signals. The ultrasound data processor is further configured to calculate synthetic aperture ultrasound images based on the ultrasound detection signals and the needle angular orientation signals.

In an embodiment, the ultrasound transducer element is a single crystal ultrasound transducer element. In an embodiment, the single crystal ultrasound transducer element is a piezoelectric (PZT) element.

In an embodiment, the needle constraining assembly constrains the needle to one angular degree of freedom about a pivot point of the needle between the proximal end and the distal end of the needle.

In an embodiment, the needle constraining assembly constrains the needle to two angular degrees of freedom about a pivot point of the needle between the proximal end and the distal end of the needle.

In an embodiment, the needle constraining assembly constrains the needle to three angular degrees of freedom such that two angular degrees of freedom are about a pivot point of the needle between the proximal end and the distal end of the needle and one angular degree of freedom is rotation about an axis of the needle.

In an embodiment, the needle constraining assembly has a configuration which allows the needle to translate along an axial direction for positioning, repositioning, advancing and withdrawing the needle. In an embodiment, the needle constraining assembly allows the needle to be moved by hand by a user. In an embodiment, the needle defines a lumen therein to allow transfer of fluids there through.

The embodiments illustrated and discussed in the above paragraphs are intended only to teach those skilled in the art how to make and use the invention. In describing embodiments of the disclosure, specific terminology is employed for the sake of clarity. However, the disclosure is not intended to be limited to the specific terminology so selected. The above-described embodiments of the disclosure may be modified or varied, without departing from the invention, as appreciated by those skilled in the art in light of the above teachings. It is therefore to be understood that, within the scope of the claims and their equivalents, the invention may be practiced otherwise than as specifically described. For example, it is to be understood that the present disclosure contemplates that, to the extent possible, one or more features of any embodiment can be combined with one or more features of any other embodiment.

We claim:

1. A needle placement system, comprising:
a needle having a proximal end and a distal end;
an ultrasound transducer element attached to the distal end of the needle;
a needle constraining assembly configured to receive and selectively constrain the needle to only rotational degrees of freedom within at least a range of angular motion;
a needle sensor system incorporated into the needle constraining assembly to sense an angular orientation of the needle; and
an ultrasound data processor configured to:
   communicate with the ultrasound transducer element to receive ultrasound detection signals,
   communicate with the needle sensor system to receive needle angular orientation signals, and
   reconstruct focused ultrasound images using or enabled by tracking information based on the ultrasound detection signals and the needle angular orientation signals,
   wherein synthetic aperture ultrasound images are calculated based on moving the ultrasound transducer element to various locations,
   wherein the ultrasound transducer element is configured to emit and receive the ultrasound detection signals at the various locations,
   wherein the tracking information comprises a determination of a spatial relationship between successive ultrasound detection signals, of the ultrasound detection signals,
   wherein the spatial relationship between the successive ultrasound detection signals is less than a wavelength divided by two, and
   wherein the wavelength corresponds to a central frequency of the ultrasound transducer element.

2. The needle placement system according to claim 1, wherein the ultrasound transducer element is a single crystal ultrasound transducer element.

3. The needle placement system according to claim 2, wherein the single crystal ultrasound transducer element is a piezoelectric (PZT) element.

4. The needle placement system according to claim 1, wherein the needle constraining assembly constrains the needle to one angular degree of freedom about a pivot point of the needle between the proximal end and the distal end of the needle.

5. The needle placement system according to claim 1, wherein the needle constraining assembly constrains the needle to two angular degrees of freedom about a pivot point of the needle between the proximal end and the distal end of the needle.

6. The needle placement system according to claim 1, wherein the needle constraining assembly constrains the needle to three angular degrees of freedom such that two angular degrees of freedom are about a pivot point of the needle between the proximal end and the distal end of the needle and one angular degree of freedom is rotation about an axis of the needle.

7. The needle placement system according to claim 1, wherein the needle constraining assembly has a configuration which allows the needle to translate along an axial direction for positioning, repositioning, advancing and withdrawing the needle.

8. The needle placement system according to claim 1, wherein the needle constraining assembly allows the needle to be moved by hand by a user.

9. The needle placement system according to claim 1, wherein the needle defines a lumen therein to allow transfer of fluids therethrough.

10. A device, comprising:
a needle having a proximal end and a distal end;
an ultrasound transducer element attached to the distal end of the needle,
   the ultrasound transducer element to send and receive ultrasound detection signals;
a needle guide configured to receive the needle so that a tip of the needle extends beyond a distal end of the needle guide;
a position encoder for determining an angular position of the needle with respect to the needle guide,
   the position encoder being disposed on the needle guide; and an ultrasound data processor configured to:
  communicate with the ultrasound transducer element to receive the ultrasound detection signals,
  communicate with a needle sensor system, incorporated into the needle guide, to receive needle angular orientation signals, and
  reconstruct focused ultrasound images using or enabled by tracking information based on the ultrasound detection signals and the needle angular orientation signals,
    synthetic aperture ultrasound images being calculated based on moving the ultrasound transducer element to various locations,
    the ultrasound transducer element being configured to emit and receive the ultrasound detection signals at the various locations,
    the tracking information comprising a determination of a spatial relationship between successive ultrasound detection signals, of the ultrasound detection signals,
    the spatial relationship between the successive ultrasound detection signals is less than a wavelength divided by two, and
    the wavelength corresponding to a central frequency of the ultrasound transducer element.

11. The device of claim 10, wherein the ultrasound transducer element is connected to a signal generation and acquisition system.

12. The device of claim 11, wherein the ultrasound transducer element is configured to send and receive the ultrasound detection signals to the signal generation and acquisition system,
  wherein the position encoder is configured to send the needle angular orientation signals to the signal generation and acquisition system,
    the signal generation and acquisition system to calculate the synthetic aperture ultrasound images based on the ultrasound detection signals and the needle angular orientation signals.

13. The device of claim 10, wherein the ultrasound transducer element is a single crystal ultrasound transducer element.

14. The device of claim 10, wherein the needle guide is configured to allow angular rotation of the needle within the needle guide.

15. The device of claim 10, wherein the needle guide is configured to allow a physician to rock the needle in an arc around a longitudinal axis of the needle.

16. The device of claim 15, further comprising:
a triggering circuit to activate the position encoder and a signal generation and acquisition system within a few microseconds or less of each other.

17. A method, comprising:
receiving, by a device, ultrasound detection signals from an ultrasound transducer element,
  the ultrasound transducer element being positioned at a distal end of a needle,
  the needle being positioned within a needle guide so that a tip of the needle extends beyond a distal end of the needle guide;
receiving, by the device, needle angular orientation signals from a position encoder,
  the needle angular orientation signals being associated with an angular rotation of the needle with respect to the needle guide; and
reconstructing, by the device, focused ultrasound images using or enabled by tracking information based on the ultrasound detection signals and the needle angular orientation signals,
  synthetic aperture ultrasound images being calculated based on moving the ultrasound transducer element to various locations,
  the ultrasound transducer element being configured to emit and receive the ultrasound detection signals at the various locations,
  a spatial relationship between successive ultrasound detection signals is less than a wavelength divided by two, and
  the wavelength corresponding to a central frequency of the ultrasound transducer element.

18. The method of claim 17, wherein the ultrasound transducer element is a single crystal ultrasound transducer element.

19. The method of claim 17, wherein the ultrasound transducer element is connected to a pulsing circuit associated with a signal generation and acquisition system.

20. The method of claim 17, wherein the position encoder is housed in a holster, and
wherein the method further comprises:
  measuring an angle of the needle and an angle of the ultrasound transducer element with respect to the holster using the position encoder.

* * * * *